US006932833B1

(12) United States Patent
Sandoval et al.

(10) Patent No.: US 6,932,833 B1
(45) Date of Patent: Aug. 23, 2005

(54) METHOD AND BARRIER FOR LIMITING FLUID MOVEMENT THROUGH A TISSUE RENT

(75) Inventors: Aaron Sandoval, Tracey, CA (US); Robert Presley, Colorado Springs, CO (US)

(73) Assignee: Bobby W. Presley, Fair Oaks Ranch, TX (US)

( * ) Notice: Subject to any disclaimer, the term of this patent is extended or adjusted under 35 U.S.C. 154(b) by 149 days.

(21) Appl. No.: 10/114,662

(22) Filed: Apr. 1, 2002

(51) Int. Cl.[7] ............................................. A61B 17/08
(52) U.S. Cl. ....................... 606/213; 606/214; 128/898
(58) Field of Search ................................ 606/213, 214, 606/61, 185; 424/422, 423, 443, 444; 128/898; 623/17.11, 17.12

(56) References Cited

U.S. PATENT DOCUMENTS

| | | | |
|---|---|---|---|
| 3,742,955 A | 7/1973 | Battista et al. | |
| 4,231,369 A | 11/1980 | Sørensen et al. | |
| 4,390,018 A | 6/1983 | Zukowski | |
| 4,890,612 A | 1/1990 | Kensey | |
| 5,053,046 A | 10/1991 | Janese | |
| 5,152,759 A | 10/1992 | Parel et al. | |
| 5,192,301 A | 3/1993 | Kamiya et al. | |
| 5,192,302 A | 3/1993 | Kensey et al. | |
| 5,192,326 A * | 3/1993 | Bao et al. ................. | 623/17.12 |
| 5,258,042 A | 11/1993 | Mehta | |
| 5,320,639 A | 6/1994 | Rudnick | |
| 5,370,660 A | 12/1994 | Weinstein et al. | |
| 5,447,502 A | 9/1995 | Haaga | |
| 5,456,693 A | 10/1995 | Conston et al. | |
| 5,486,195 A | 1/1996 | Myers et al. | |
| 5,571,181 A | 11/1996 | Li | |
| 5,573,519 A | 11/1996 | Zohmann | |

(Continued)

FOREIGN PATENT DOCUMENTS

EP 0 493 810 A1 7/1992

OTHER PUBLICATIONS

Bailey, Orville T. and Ingraham, Franc D., "Fibrin Films in Neurosurgery, with Special Reference to Their Use in the Repair of Dural Defects and in the Prevention of Meningo-cerebral Adhesions," Harvard Medical School, Feb. 17, 1944, Paper No. 27, pp. 597-600.

(Continued)

Primary Examiner—Julian W. Woo
(74) Attorney, Agent, or Firm—Bill Kennedy; Haynes Beffel & Wolfeld LLP

(57) ABSTRACT

A method and device provides for limiting fluid movement through a rent in a membranous tissue by forming a biocompatible and biodegradable barrier at the site of the rent. The barrier is formed by inserting into the rent a plug that includes connected water-swellable parts, so that within a short time following placement of the plug at the site the swellable parts expand in situ to form the barrier and occlude the rent. As fluids near the site are taken up by the swellable material, the material expands rapidly to fill the rent, engaging the marginal surfaces of the membrane near the edges of rent and forming a secure barrier at the site. All the materials of the plug are biocompatible and, over a period of time that allows for healing of the rent, all the components of the barrier are completely degraded without leaving any residual material at the site.

20 Claims, 8 Drawing Sheets

U.S. PATENT DOCUMENTS

| | | | |
|---|---|---|---|
| 5,628,734 | A | 5/1997 | Hatfalvi |
| 5,634,936 | A | 6/1997 | Linden et al. |
| 5,643,318 | A | 7/1997 | Tsukernik et al. |
| 5,649,959 | A | 7/1997 | Hannam et al. |
| 5,725,551 | A | 3/1998 | Myers et al. |
| 5,733,545 | A | 3/1998 | Hood, III |
| 5,782,860 | A | 7/1998 | Epstein et al. |
| 5,834,029 | A | 11/1998 | Bellamkonda et al. |
| 5,861,003 | A | 1/1999 | Latson et al. |
| 5,902,832 | A * | 5/1999 | Van Bladel et al. ........ 424/423 |
| 5,904,703 | A | 5/1999 | Gilson |
| 5,922,009 | A | 7/1999 | Epstein et al. |
| 5,951,589 | A | 9/1999 | Epstein et al. |
| 5,976,174 | A | 11/1999 | Ruiz |
| 5,989,215 | A | 11/1999 | Delmotte et al. |
| 5,997,895 | A | 12/1999 | Narotam et al. |
| 6,022,361 | A | 2/2000 | Epstein et al. |
| 6,045,570 | A | 4/2000 | Epstein et al. |
| 6,056,769 | A | 5/2000 | Epstein et al. |
| 6,056,770 | A | 5/2000 | Epstein et al. |
| 6,074,663 | A | 6/2000 | Delmotte et al. |
| 6,096,021 | A | 8/2000 | Helm et al. |
| 6,177,095 | B1 | 1/2001 | Sawhney et al. |
| 6,183,498 | B1 | 2/2001 | Devore et al. |
| 6,268,405 | B1 | 7/2001 | Yao et al. |
| 6,274,090 | B1 | 8/2001 | Coelho et al. |
| 6,296,657 | B1 | 10/2001 | Brucker |
| 6,319,263 | B1 | 11/2001 | Levinson |
| 6,334,865 | B1 | 1/2002 | Redmond et al. |
| 6,352,710 | B2 | 3/2002 | Sawhney et al. |
| 6,395,292 | B2 | 5/2002 | Peery et al. |
| 6,447,534 | B2 | 9/2002 | Cragg et al. |
| 6,514,271 | B2 * | 2/2003 | Evans et al. ................ 606/185 |
| 2001/0046518 | A1 | 11/2001 | Sawhney |
| 2002/0120276 | A1 | 8/2002 | Greene, Jr. et al. |
| 2002/0165581 | A1 | 11/2002 | Brucker |
| 2003/0014075 | A1 | 1/2003 | Rosenbluth et al. |
| 2003/0109899 | A1 | 6/2003 | Fisher et al. |

OTHER PUBLICATIONS

Hadley, M. N., Martin, Neil A., Spetzler, Robert F., Sonntag, Volker K. H., and Johnson, Peter C., "Comparative Transoral Dural Closure Techniques: A Canine Model," Neurosurgery, 1988, vol. 22, No. 2, pp 392-397.

Keating, Robert F. and Potter, Paul, "Tethered Cord Dural Repair with Intraoperative Autologous Fibrin Glue," Presented at American Association of Neurological Surgeons Pediatric Session. Vancouver, Canada, Dec. 1992, pp. 2-6. [Abstract at least].

Schier, F., Srour, N., and Waldschmidt, J., "Dura Covered with Fibrin Glue Reduces Adhesions in Abdominal Wall Defects," European Jour. Pediatric Surgery 1 (1991), pp343-345.

Toma, Abbad G., Fisher, Edward W., and Cheesman, Anthony D., "Autologous Fibrin Glue in the Repair of Dural Defects in Craniofacial Resections", Jour. of Laryngol. Otol., Apr. 1992, vol. 106, pp 356-357.

Wiegand, David A., Hartel, Maria I., Quander, Troy, Latz, Barbara, and Dankle, Jon A., "Assessment of Cryoprecipitate-Thrombin Solution for Dural Repair," Head and Neck, Nov./Dec. 1994, pp. 569-573.

* cited by examiner

METHOD AND BARRIER FOR LIMITING FLUID MOVEMENT THROUGH A TISSUE RENT

BACKGROUND

This invention relates to limiting fluid movement through rents in body tissues, and particularly the invention relates to providing a barrier for fluid movement through a puncture in a membranous tissue such as the dura mater.

For many medical procedures, access to an internal body cavity is made by way of a puncture or other opening in the wall or membrane enclosing the body cavity. Following such a procedure, fluids or fluid-borne materials may pass through the opening or rent, and complications may result. Reliable methods are needed for limiting movement of fluids or fluid-borne materials across openings in membranes enclosing body cavities, to mitigate such complications.

The mammalian brain and spinal cord are closely invested by a membrane termed the pia mater, and are surrounded by a thick inelastic membrane termed the dura mater. A delicate membrane termed the arachnoid envelops the brain and spinal cord between the dura mater and the pia mater. The arachnoid is separated from the pia mater by the so-called intrathecal or subarachnoid space, which is filled with cerebrospinal fluid ("CSF"). The intrathecal space is accessed clinically, usually by a percutaneous needle puncture through the dura, for a wide variety of purposes, including collection of CSF for chemical and cytological analysis and delivery of therapeutic agents. Percutaneous needle puncture through the dura is one of the most common procedures performed in clinical medicine.

Intraspinal administration of anesthetics and analgesics has been performed for over one hundred years; it has in recent years come into increasing use in obstetrics, urology, and orthopedics, and it is now a mainstay of therapy in the rapidly growing field of pain management.

Diagnostic myelography is commonly employed prior to all types of spinal surgery, entailing injection of radiographic contrast material into the intrathecal space. The intrathecal space also provides a depot for administration of chemotherapy, and rapid advances in neurobiology promise a range of new therapies directed at degenerative central nervous system conditions. Diseases such as multiple sclerosis, amyelotrophic lateral sclerosis (Lou Gehrig's disease), Alzheimer's disease, and others, will likely generate increased need for intrathecal access to permit delivery of drugs that may not easily cross the blood-brain barrier.

Headache is the most common complication of dural puncture. The pathogenesis of post dural puncture headache (PDPH) is generally believed to be related to ongoing CSF leak at the site of the dural puncture, although the mechanism of pain is not clear. Low CSF pressure may result in traction on pain sensitive structures, especially where the subject is in the upright position, caused by loss of the cushioning effect of the normal CSF volume. Vascular dilatation in response to low CSF volume may also be a factor, and neurohumeral responses have been implicated as well. Whatever the cause or causes may be, the reported incidence of PDPH ranges from two percent to 75 percent, depending on a variety of epidemiological factors, including the age, gender, and medical condition of the patient. Women are more likely than men to suffer PDPH, and the rate of PDPH is more likely in younger than in older adults; and it is therefore unsurprising that PDPH is a significant problem following spinal anesthesia in the obstetrical population.

Technical factors may play an important role in generation of PDPH, including needle diameter, needle tip configuration, preparation of the skin, and characteristics of injected material. Incidence of PDPH can be reduced by employing a smaller needle (gauge 25 or higher) or by employing a needle having a "pencil tip" with a side port; and some practitioners have recommended orienting the needle in parallel with the dural fibers. The use of small needles as an approach to reducing the occurrence of PDPH is limited by the greater technical difficulty (especially for non-anesthesiologists) of achieving successful dural puncture using smaller needles; and viscosity of some injectates (myelography dies, for example) is too high to permit the use of smaller needles. Even where optimal technique is employed in low risk populations, the incidence of PDPH is reported as five to 20 percent or more in most studies.

The pain due to PDPH is typically severe and long-lasting, and it can be completely disabling in some instances for days to weeks following the dural puncture procedure. PDPH pain can be relieved by maintaining the subject in a supine position, and patients often are confined to bed for the duration of the headache episode. Symptoms associated with PDPH include nausea and vomiting which predisposes the patient to dehydration and impairs the patient's ability to replace lost CSF, prolonging the painful syndrome. Visual disturbances, tinnitus, vertigo, neck stiffness and auditory symptoms all contribute to the disability associated with PDPH. Severe traction on cranial nerves resulting from low CSF pressure can cause significant palsy, particularly of the with cranial nerve. Traction on intracranial vascular structures can result in potentially fatal intracranial hemorrhage, although this complication is rare. The typical onset of PDPH is 24–48 hours after the procedure, with a duration of three to four days, and approximately 75 percent of patients experience resolution of symptoms within seven days after onset, although it is not unusual for PDPH to last for weeks.

Types of treatment for PDPH generally fall into two categories. Nonspecific, supportive therapies including correction of dehydration and administration of analgesics and anti-emetics are generally sufficient for mild PDPH, in conjunction with maintenance of a supine position at bed rest. Corrective therapies include treatments designed to increase CSF volume and obtund the neurohumeral or vascular cause of the headache. Methylxanthenes such as caffeine and theophylline can constrict cerebral venous channels and promote CSF production, and such agents are often sufficient to control mild cases of PDPH.

The definitive treatment for PDPH, however, is to stop the leak by performing an epidural blood patch. This involves drawing 10–20 cc of sterile autologous blood and administering the blood via a standard epidural access procedure at the same spinal level. In theory, the blood patch halts the flow of CSF from the intrathecal space, reversing the pressure gradient from lumbar spine to cranial vault, and pushes the remaining CSF toward the brain to provide support for the intracranial structures, thereby producing immediate relief. The success rate of the dural blood patch in mitigating PDPH is reported as 85–95 percent. Complications from the dural blood patch procedure are unusual, other than mild low back discomfort and stiffness, but there are case reports of subdural hematoma, abscess formation, arachnoiditis, and even blindness following repeat epidural blood patch. Attempts to employ an epidural blood patch prophylactically have uniformly failed to mitigate PDPH. And the epidural blood patch procedure is highly costly from an economic standpoint.

Accordingly, PDPH continues to be a very troublesome complication of otherwise successful intrathecal access by dural puncture, which may have important implications for the patient's post-operative course. For instance, PDPH following cesarean section results in poorer maternal-infant bonding and inability to breast-feed. Diagnostic lumbar puncture is frequently performed for diagnosis of headache, for example to rule out meningitis, and the presence of PDPH may seriously confound efforts and diagnosis. PDPH is very costly in terms of lost days at work and diminished productivity, and additional days of hospitalization, economically burdening the patient and the employer as well as the health care and health insurance systems.

A need persists for a method of reliably preventing PDPH as a complication of dural puncture procedures.

SUMMARY

The invention provides for limiting fluid movement through a rent in a membranous tissue by forming a biocompatible and biodegradable barrier at the site of the rent. According to the invention, the barrier is formed by inserting into the rent a plug that includes connected water-swellable parts, so that the swellable parts expand in situ to form the barrier and occlude the rent.

The invention can be employed in connection with any of the many procedures in which access to an internal body space is made by way of a puncture in a wall or membrane. Particularly, for example, the invention can be employed prophylactically at the conclusion of a conventional dural access procedure.

The materials of which the plug is made are biocompatible. Generally, as deployed according to the invention, the plug materials do not cause significant cell injury or death; they do not cause an adverse inflammatory response; and they do not cause malignant cellular transformation.

The materials of which the plug is made are biodegradable. Generally, the plug materials are capable of being broken down and removed from the site by normal physiologic and cellular processes within the body of the subject being treated, typically including for example dissolution in the aqueous environment, leukocyte/macrophage macrocytosis, and enzymatic digestion. The degradation products are metabolized or transferred away from the site ultimately through venous and lymphatic channels. Preferably the degradation products and their metabolites are also biocompatible. The plug or barrier materials do not persist permanently at the site, and degradation and removal of residues of the material proceeds to completion over a course of time of weeks or months.

Plugs according to invention can be configured and dimensioned to form barriers in rents having a wide range of dimensions and shapes, and in membranes or walls having a wide range of thicknesses. The swellable parts are provided in a shape and size appropriate to the shape and size of the particular rent.

A plug according to the invention can be deployed by using a stylet to pass the plug within the lumen of a needle or catheter to a point just beyond the tip. The needle or catheter is then withdrawn over the stylet and the plug is left in place at the puncture site. As fluids near the site are taken up by the swellable material, the material expands rapidly to fill the rent, engaging the marginal surfaces of the membrane near the edges of rent and forming a secure barrier at the site. All the materials of the plug are biocompatible and, over a period of time that allows for healing of the rent, all the components of the barrier are completely degraded without leaving any residual material at the site.

Accordingly, in one general aspect the invention features a method for limiting fluid movement through a rent in a membranous tissue, by placing within the rent a plug that includes connected water-swellable parts, so that the swellable parts expand in situ to occlude the rent. In some embodiments, the plug includes two swellable parts joined by a connector, and the placement of the plug according to invention includes positioning the plug so that one swellable part is within a volume bounded by one surface of the membranous tissue and the other swellable part is within a volume bounded by the opposite surface of the membranous tissue, and the connector traverses the rent.

The method can be particularly useful for forming a barrier in a rent in the dura mater. The method can be employed for management of an intraspinal dural rent, or of an intracranial dural rent; including management of a rent at any point in the spinal dura (cervical, thoracic, lumbar, sacral), at any point along the spine from C1 to the sacrum, and including management of a puncture made at the foramen magnum for a CSF tap. For closing a rent (such as a puncture) in the spinal dura, for example, the plug is positioned in the rent so that one swellable part is within the subarachnoid space, and the other swellable part is positioned in the epidural space, and the connector traverses the puncture in the dura. Over a brief time (in the order of seconds to minutes) the parts swell in situ, so that the swollen parts fill the opening in the dura and engage the margin at the edge of the opening, forming the fixed barrier at the site. Thereafter, over a longer time (in the order of days to weeks or months), the barrier is degraded as the rent heals, so that eventually the opening is closed and nothing remains of the barrier.

In some embodiments, the placement of the plug according to the method includes passing the plug through the lumen of a needle or catheter. For treating a puncture in the spinal dura, for example, the plug is placed by pushing it through the dural puncture needle.

The invention can be employed prophylactically at the conclusion of the dural puncture procedure, to occlude the dural defect and thereby inhibit the movement of CSF out from the intrathecal space and the movement of potentially complicating substances into the CSF through the rent. Deployment of the plug through the dural puncture needle provides a dural rent management protocol that is highly reliable and reproducible. Because the size of the dural defect is related to the diameter of the dural puncture needle, sizing the plug according to the lumenal diameter of the needle can index and appropriate size for the barrier that results from swelling of the plug in situ following withdrawal needle over the plug. The rent management protocol according to the invention does not require an additional skill set for the operator beyond confidence in performing the dural puncture itself, and requires only minimal elongation of the dural access procedure.

The plug materials according to the invention are selected for use in regions of the body for which their capacities for biocompatibility and biodegradability are well known or readily ascertainable.

Plugs in a variety of lengths and diameters can be included in a spinal access tray or kit currently in use, without significant dedication of the current configurations of the tray or kit. No special apparatus is needed for carrying out the method of the invention and, accordingly, the invention provides for a cost effective and convenient approach to dural defect management that features a high level of reliability and safety and a low potential for complication.

In another general aspect the invention features a biocompatible and biodegradable plug body for insertion into a tissue rent to form a barrier to fluid movement through the rent, having a swellable portion including at least two connected water-swellable parts. In some embodiments the water-swellable parts are end portions of a dumbbell-shaped body formed entirely of a water-swellable material; in some embodiments the water-swellable parts are beads formed on a connecting filament.

In order to form an effective barrier, the swellable portion of the plug swells in situ from a size small enough that it can be deployed within the rent to a size sufficiently large that the swelled portions engage the membrane or wall near the edges of the rent, and thereby secure the barrier at the site. Accordingly, the material of which the swellable parts are formed is selected so that the swellable parts can increase in size in an aqueous medium (such as, for example, in a physiological saline at about normal body temperature, comparable to conditions at the site in the body of the subject being treated) at least 1.2 times in a transverse dimension, and in some embodiments as much as 10 times in a transverse dimension. In some embodiments swellable parts can increase in size in an aqueous medium to at least 1.3 times, in some embodiments at least 2 times; and as much as 5 times, still more usually as much as 3 times. In particular embodiments the swellable parts increase in size in an aqueous medium about 1.2–3 times in a transverse dimension.

In some embodiments the material of which the swellable parts are formed includes a biocompatible and biodegradable water-swellable polymer. The water-swellable polymer may be protein-based, or carbohydrate-based, or mineral-based. In some embodiments the water-swellable polymer is a gelatin, a collagen, a cellulose, an agarose, a hyaluronic acid, a poly(vinyl alcohol) (PVA), a poly(ethylene oxide) (PEO), or the like. The material of which the swellable parts are formed can be a foamed gel, or a sponge or mesh, or the like.

In some embodiments the connecting filament is formed of a biocompatible and biodegradable non water-swellable material, such as a polyglycolate or a polylactate or a polydioxanone, or the like. Preferably the filament is a monofilament, rather than a multifilament. Conveniently the connecting filament can be formed of an absorbable suture material, that is, a sterile filament prepared from collagen derived from a healthy mammal, or a synthetic polymer, capable of being biodegraded by living mammalian tissue.

In some embodiments the beads have a generally spheroidal or spherical or ovoid shape; in some embodiments the beads are discoid in shape; in other embodiments the beads are elongated in an axial direction. The beads need not be separate from one another, and in some embodiments the swellable material is continuous between adjacent beads.

In some embodiments, where the plug is to be deployed through a needle or catheter, the swellable parts are sized small enough in a dimension transverse to the filament axis so that they can be passed readily within the lumen of the particular needle or catheter.

In some embodiments the swellable portion of the plug has a length at least 6 millimeters, and more usually at least 10 millimeters; and in some embodiments the swellable portion of the plug has a length at most 20 millimeters, and more usually at most 12 millimeters; in particular embodiment, for use for example in management of an intraspinal dural rent, the swellable portion of the plug has a length in the range 10 to 12 millimeters.

Where the plug is to be deployed by passing it through the lumen of a needle or catheter, the inside diameter of the deployment tool imposes a limit on the wider transverse dimension (for example, the transverse diameter) of the swellable parts of the plug. The inside diameter of a thin-walled 15 gauge needle, for example, may typically be about 1.5 millimeters, requiring that a plug to be deployed through such a needle have a maximum transverse dimension less than about 1.5 millimeters; and the inside diameter of a thin-walled 27 gauge needle, for example, may typically be about 0.2 millimeters, requiring that a plug to be deployed through such a needle have a maximum transverse dimension less than about 0.2 millimeters.

In some embodiments the swellable parts are pitched closely enough together to enable any adjacent two of them to engage the margin at the edge of the rent as they swell. And in some embodiments they are pitched at a distance apart at least equal to about the thickness of the membrane or wall that they are intended to traverse, to ensure that an adjacent pair of the swellable parts can span the thickness at the rent.

In some embodiments the connecting filament is sufficiently stiff that it can serve as a stylet, and in such embodiments the filament may extend well beyond the water swellable beaded portion. The stiffness of the filament will be characteristic of the material and the thickness of the filament.

The invention can be employed in conjunction with any of a variety of medical procedures during which an internal body space is accessed by puncture or rent through a wall or membrane.

The invention can also be employed in conjunction with any of a variety of medical procedures in which a puncture or rent is formed unintentionally. For example, the spinal dura may be unintentionally punctured by the epidural needle in the course of preparing to administer an anesthetic into the epidural space; according to the invention, loss of CSF from the intrathecal space and movement of anesthetic into the intrathecal space can be limited by forming a barrier in such a dural rent prior to completion of the procedure.

DETAILED DESCRIPTION

The invention will now be described in further detail by reference to the drawings, which illustrate alternative embodiments of the invention. The drawings are diagrammatic, showing features of the invention and their relation to other features and structures, and are not made to scale. For improved clarity of presentation, in the Figs. illustrating embodiments of the invention, corresponding elements shown in the various drawings are not all particularly renumbered, although they are all readily identifiable in all the Figs. Certain anatomical and histological features, not necessary to an understanding of the invention, are omitted from the Figs.

Figure 1:
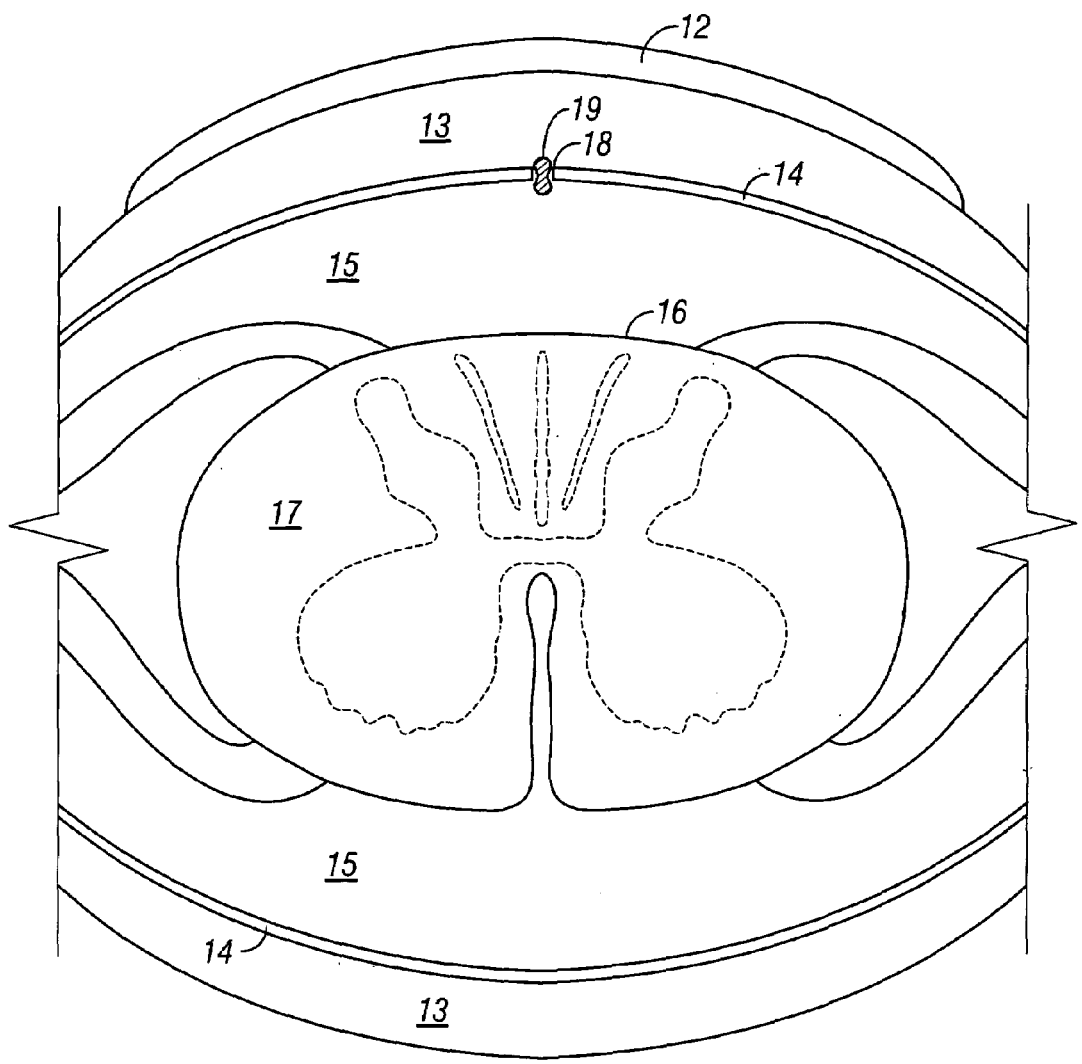
FIG. 1 is a diagrammatic sketch in a transverse sectional view thru a portion of the spine of a subject showing a plug in place according to the invention at a dural puncture site.

Turning now to FIG. 1, there is shown a diagrammatic sectional view thru the spinal cord and associated structures, immediately following placement of a plug according to the invention within a puncture in the dura mater. The spinal dura mater 14 forms a sheath around the spinal cord 17. The spinal dura is underlain at its inner surface 21 by the arachnoid and the spinal cord is invested on its outer surface 16 by the pia mater. An epidural space 13 separates the dura 14 from the vertebral canal, defined at the level of the sectional view of FIGS. 1 and 2 by the vertebral body and, dorsally, by the ligamentum flavum 12. The arachnoid is separated from the pia mater by the subarachnoid space 15, which is filled with cerebrospinal fluid.

Access to the subarachnoid space 15 can be obtained by passing a needle or catheter (not shown in FIG. 1 or 2) through the intervertebral space between adjoining vertebrae. The needle or catheter penetrates through the skin and subcutaneous fatty tissues (not shown in the Figs.), through the ligamentum flavum 12, through the epidural space 13, and through the dura 14 into the subarachnoid space 15. When the needle or catheter is withdrawn, an opening or rent 18 remains in the dura at the site of the puncture.

Figure 2:
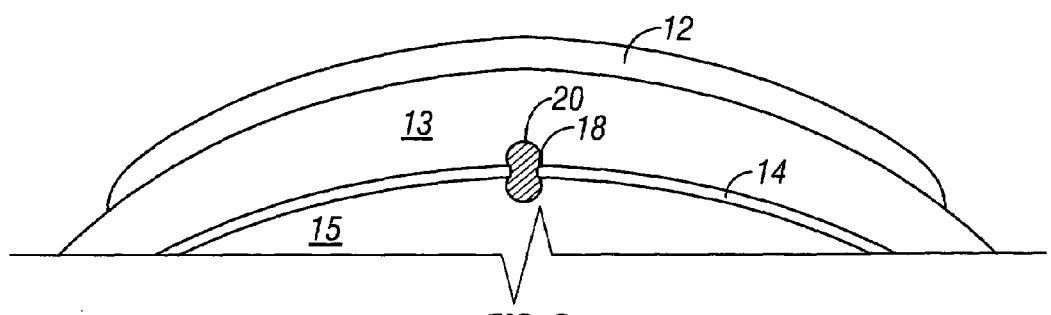
FIG. 2 is a diagrammatic sketch of a portion of a sectional view as in FIG. 1, showing a barrier at the dural puncture site formed by swelling of the plug according to the invention.

According to the invention, a biocompatible and biodegradable plug 19 is placed at the site of the rent. At least part of the plug 19 is swellable in tissue fluids, and, after a short time generally in a scale of seconds or minutes, the plug swells in situ to form a barrier 20 that occludes the rent, as shown in FIG. 2. The plug is gradually degraded over a time sufficient to permit the rent to close by healing.

Some exemplary embodiments of plugs and of barriers formed in situ by swelling of the plugs according to the invention are shown in FIGS. 3–5, 6–8, 9–11, and 12–18.

Figure 3:
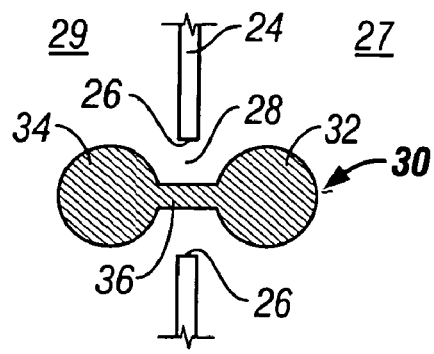
FIG. 3 is a diagrammatic sketch in a lengthwise sectional view thru a plug in place at a dural puncture site according to an embodiment of the invention.
Figure 4:
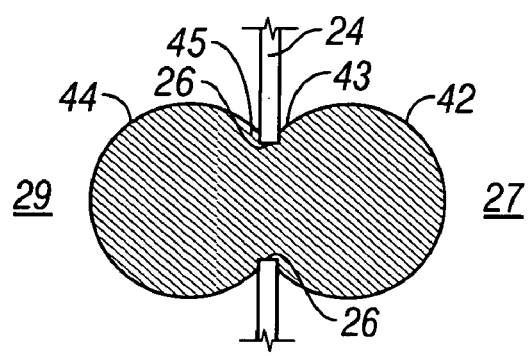
FIG. 4 is a diagrammatic sketch in a lengthwise sectional view showing a stage in the formation of a barrier from the plug of FIG. 3.
Figure 5:
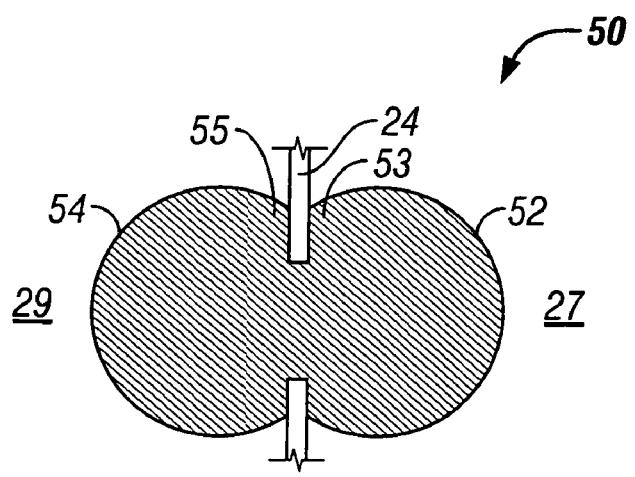
FIG. 5 is a diagrammatic sketch in a lengthwise sectional view thru a barrier formed at the site of a dural puncture from the plug of FIG. 3.

In the embodiment of FIG. 3, for example, the plug 30 has a dumbbell shape, with a pair of wider parts 32, 34 joined by a narrower connecting part 36. The plug is placed at the site of the rent 28 such that one wider part 32 is in the volume 27 bounded by one surface of the membrane 24 and the other wider part 34 is within the volume 29 bounded by the other surface of the membrane 24, and the connecting part 36 traverses the rent 28. In this embodiment the connecting part as well as the larger parts are made of a swellable material. Within a short time following placement of the plug at the site of the rent (typically in the order of a few seconds) the material swells to engage the edge 26 of the rent 28, occluding the opening. Particularly, as shown in FIG. 4, the medial regions 43, 45 of the wider parts 42, 44 swell against the surfaces of the membrane 24 at the edge 26 of the rent. FIG. 5 shows a barrier 50 resulting from the continued swelling of the plug material at the site of the rent. Here the medial regions 53, 55 of the swollen wider parts 52, 54 engage the surfaces of the membrane at the margin of the rent, securing the barrier and preventing it from migrating away from the site. The barrier effectively obstructs movement or migration of fluids in either direction from one of the volumes 27, 29 to the other across the rent.

Suitable swellable materials include biocompatible and biodegradable water-swellable polymers, including for example hydrogels. The swellable material may be of biological origin, either derived from biological tissues or made biosynthetically; or it may be of nonbiological origin. Suitable materials include gelatins, collagens, celluloses, agaroses, hyaluronic acid (HA), poly(vinyl alcohol) (PVA), polyethylene oxide (PEO), and the like. Where the material is of biological origin it must be substantially free of active infectious agents, including particularly viruses and prions. The swellable material can be a foamed gel, or a sponge, or a nonwoven mesh or felt, or the like. As one example, a foamed gelatin material distributed by Pharmacea and Upjohn under the name "GELFOAM®" may be particularly useful as a swellable material according to the invention.

The swellable material may include combinations of constituents that slow or accelerate the swell rate, or increase or decrease the swell capacity to suit a particular use. And the swellable material may include combination of constituents that make the initially wetted surface of the material more slippery, so that it can be more easily passed through the lumen of a needle or catheter.

Figure 6:
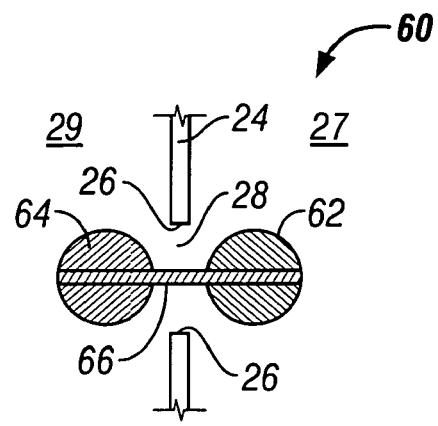
FIG. 6 is a diagrammatic sketch in a lengthwise sectional view thru a plug in place at a dural puncture site according to another embodiment of the invention.
Figure 7:
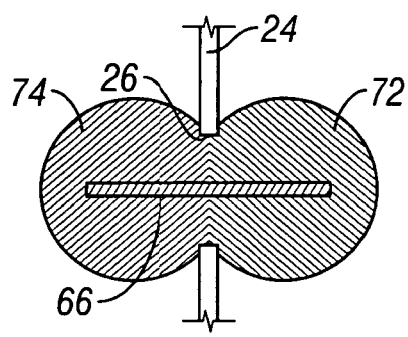
FIG. 7 is a diagrammatic sketch in a lengthwise sectional view showing a stage in the formation of a barrier from the plug of FIG. 6.
Figure 8:
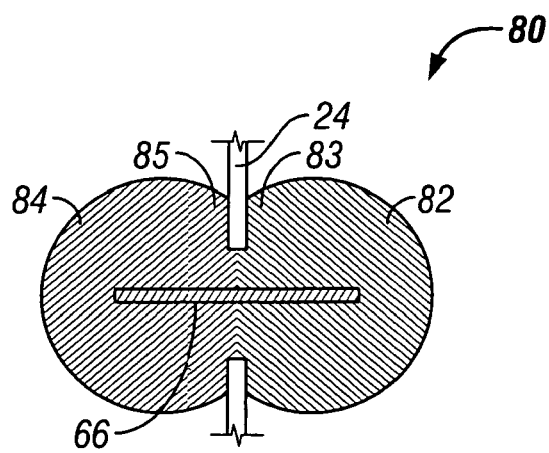
FIG. 8 is a diagrammatic sketch in a lengthwise sectional view thru a barrier formed at the site of a dural puncture from the plug of FIG. 6.

The connecting part of the plug may be made of a material different from that of the wider parts, and particularly, the connecting part may be made of a non water swellable material. In the embodiment of FIG. 6, for example, the plug 50 has a dumbbell shape, with a pair of wider parts 62, 64 of a swellable material formed on a filament 66 of a non swellable material. The plug is placed at the site of the rent 28 such that one swellable wider part 62 is within the volume 27 bounded by one surface of the membrane 24 and the other swellable wider part 64 is within the volume 29 bounded by the other surface of the membrane 24, and 80 portion of the filament 66 between the connected swellable parts traverses the rent 28. Shortly, the swellable parts 72, 74 swell to engage the edge 26 of the rent 28, occluding the opening, as shown in FIG. 7. As shown in FIG. 8, a barrier 80 is formed as a result of the continued swelling of the plug material at the site of the rent. Here, the medial regions 83, 85 of the swollen parts 82, 84 engage the surfaces of the membrane at the margin of the rent, securing the barrier, generally as described with reference to FIG. 5.

Conveniently, a plug as shown in FIG. 6 is constructed by affixing a number of swellable parts onto a filament at intervals as if attaching beads on a strand, and then trimming the filament to form pairs of swellable parts 62, 64 on a connecting part 66. In one example, a dry foamed gelatin material may be cut to an appropriate size and then mechanically compressed about the filament. The filament forming the connecting part can be provided, for example, as a sterile strand prepared from collagen derived from healthy mammal (for example from bovine gut serosa); or a synthetic polymer, such as a polyglycolate, or a polylactate, or a polydioxanone, or the like. The filament may be treated to modify its stiffness, or its resistance to absorption, or its tendency to wick; it may be impregnated or coated with a suitable antimicrobial agent; or it may be colored by an approved color additive. Particularly, the filament can be a conventional absorbable suture material.

As will be appreciated, the strength and stiffness of such a filament will depend upon mechanical properties of the filament material and upon the thickness (diameter; gauge) of the filament. In an embodiment as in FIG. 6, for example, the connecting function does not demand that the filament be particularly strong or stiff. Any conventional suture material in any conventional suture gauge, for example, would be expected to have sufficient tensile strength to maintain the connection of the two swellable parts; and the plug need be only sufficiently stiff to maintain its orientation with respect to the rent during the earlier phase of swelling.

Figure 9:
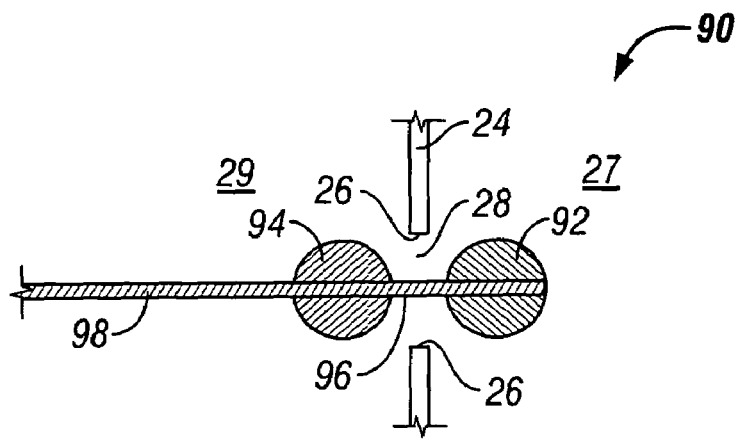
FIG. 9 is a diagrammatic sketch in a lengthwise sectional view thru a plug in place at a dural puncture site according to yet another embodiment of the invention.
Figure 10:
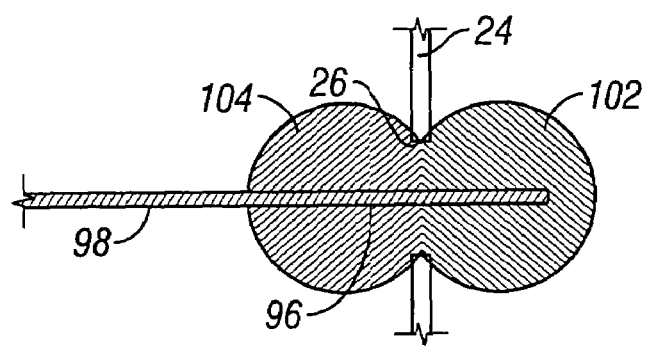
FIG. 10 is a diagrammatic sketch in a lengthwise sectional view showing a stage in the formation of a barrier from the plug of FIG. 9.
Figure 11:
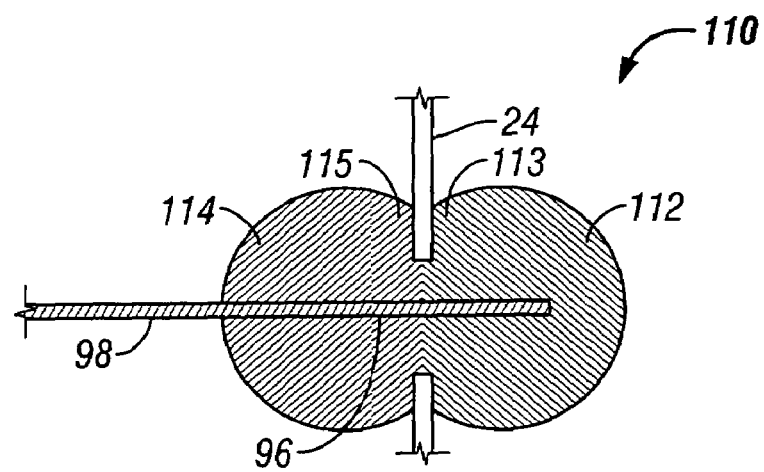
FIG. 11 is a diagrammatic sketch in a lengthwise sectional view thru a barrier formed at the site of a dural puncture from the plug of FIG. 9.

However, the placement of the plug at the site of the rent may be facilitated by providing a stiffer filament. In some embodiments of the invention, as shown by way of example in FIG. 9, the plug 90 has swellable parts 92, 94 affixed on a filament 96 as in the example of FIG. 6; but here, the filament is preferably stiff and some length 98 of the filament is left intact, to provide for ready manipulation of the plug during placement. The length 98 of the filament can serve, for example, as a stylet to guide the plug through tissues along a path to the site of the rent. And, for example, the length 98 of the filament can serve to guide the plug within the lumen of a needle of catheter toward the site of the rent. In other respects the plug 90 of FIG. 9 is similar to the plug 60 of FIG. 6, and plug 90 forms a barrier 110 through stages of swelling in a manner generally analogous to that illustrated in FIGS. 7 and 8. The swellable parts of plug 90 swell so that they 102, 204 engage the edge 26 of the rent as shown in FIG. 10 and swell further so that medial regions 113, 115 of swollen parts 112, 114 engage the surfaces of the membrane at the margins of the rent, securing the barrier 110, as shown in FIG. 11.

FIGS. 1, 3, 6 and 9 illustrate plug embodiments have a single pair of connected swellable wider portions, and for simplicity of presentation the plug is shown as being symmetrically disposed within the rent. It is not necessary that the plug be placed so that the plug axis (defined generally as a line running lengthwise through the connecting part) be oriented perpendicularly with respect to the membrane, nor that the plug axis be centered within the rent. Nor is it necessary that the plug be placed so that the two wider parts are equally distant from the plane of the rent. Orientation of the plug axis away from perpendicularity and out of center, and asymmetrical disposition of the wider parts with respect to the plane of the rent, are acceptable because the swelling plug will tend to adjust its position within the rent as the wider parts swell to engage the membrane at the edge of the rent.

However, in order for a barrier to form successfully according to the invention, occluding the rent as shown in FIGS. 2, 5, 8 and 11, the plug must be placed so that the two wider portions are located on opposite sides of the membrane. If such a plug be advanced too far or not far enough, so that both swellable parts are in a space within the membrane or outside it, the wider parts will not engage the edge of the rent as they swell, and no barrier will form at the rent.

In some instances, the rent site is hidden from view, and access to the rent site is by way of the lumen of a needle or a catheter, or by way of a path formed by a probe or blade. In such circumstances direct inspection of the site cannot be employed to ensure that the plug is advanced to an appropriate position within the rent. For example, no method is currently available for visualizing the rent site in a spinal dural puncture. Where the distance of the rent site from the insertion point at the surface of the subject's skin is known with sufficient accuracy, appropriate placement may be made for example by employing an insertion stylet having length indicia or, for an embodiment such as in FIG. 9, by employing length indicia on the extended length of the filament, and orienting the length indicia to the skin surface. Or, where the plug is inserted through a catheter or needle, length indicia on the stylet or filament can be aligned with indicia on the catheter or needle to establish the position of the plug in relation to the needle or catheter tip. So long as the position of the tip of the needle or catheter with respect to the membrane can be known with sufficient accuracy, the plug may in some such embodiments be placed appropriately by ejecting it from the tip of the stylet prior to withdrawal of the stylet or the needle. Or, in other such embodiments where an extended length of the filament serves as a stylet, the plug is left in place and the needle or catheter is withdrawn over the stylet. The use of length indicia is well known for stylets, needles, catheters, cannulae and the like.

Alternatively, in some procedures where the rent is formed by a needle or catheter or the like, it may be possible to visualize the rent site more directly. For example, in preparation for a cranial dural puncture, a portion of the skull is removed near the site, so that the dura is exposed to view. In such instances a direct visual check on the placement of the plug may be made.

As may be appreciated, where the plug has two connected swellable portions, increasing the distance between the wider parts can increase the likelihood that the plug will be appropriately placed with the connecting portion traversing the rent. The degree to which the wider parts can swell is limited, however, by the properties of the swellable material and, accordingly, the extent to which the wider parts may be separated is also limited: if they are too far apart, then the swollen parts cannot securely engage the membrane surfaces at the margin of the rent, and no barrier will be formed.

Figure 16:
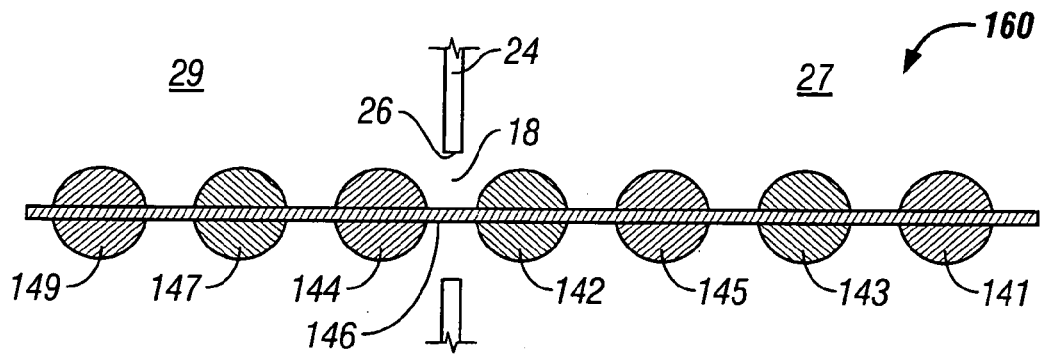
FIG. 16 is a diagrammatic sketch in a lengthwise sectional view thru a plug in place at a dural puncture site according to yet another embodiment of the invention.
Figure 17:
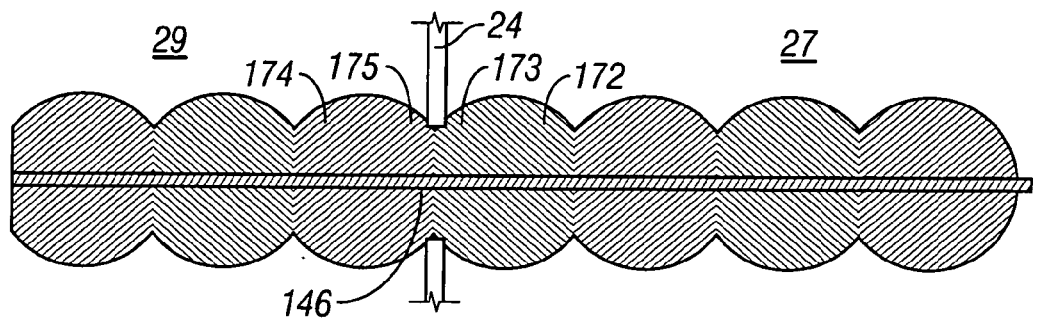
FIG. 17 is a diagrammatic sketch in a lengthwise sectional view showing a stage in the formation of a barrier from the plug of FIG. 16.
Figure 18:
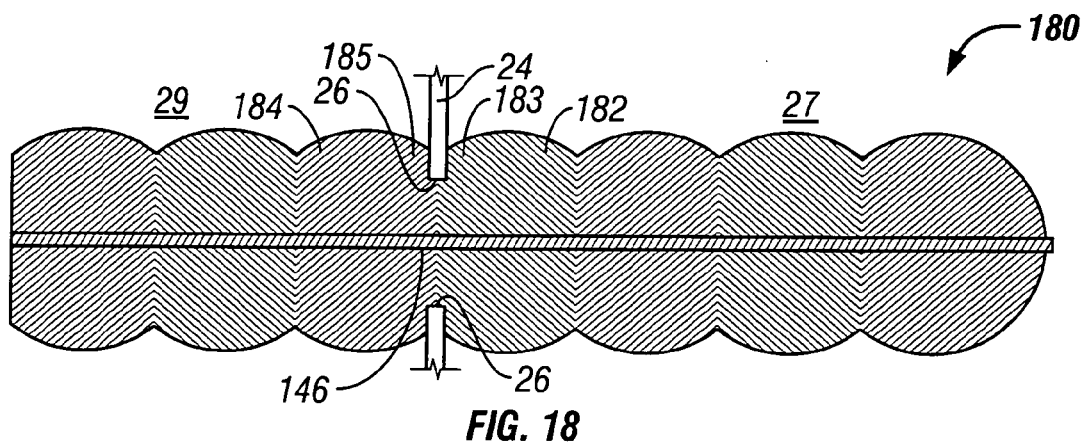
FIG. 18 is a diagrammatic sketch in a lengthwise sectional view thru a barrier formed at the site of a dural puncture from the plug of FIG. 16.

Alternatively, according to the invention, in some embodiments the plug has more than two wider swellable parts arranged in a string. This configuration increases the overall length of the swellable portion of the plug without increasing the spacing between pairs of wider swellable parts, and it improves the likelihood that when the plug is placed at the rent site, a connected pair of wider swellable parts will be appropriately placed. For instance, where three wider swellable parts are provided, the overall length of the swellable portion is double the length of a single pair of similarly spaced swellable parts; and either of two connecting pairs of swellable parts can find an appropriate location. Reference is made to FIG. 16, showing a plug 160 having several swellable parts, seven of which (141, 143, 145, 142, 144, 147 and 149) are shown in the Fig., arranged as beads on a filament 146. The plug 160 is inserted through the rent 18 and placed such that at least the most distal one 141 of the swellable parts is known with a reasonable certainty to be within the volume 27 on one side of the membrane 24, and such that at least one more proximal swellable part, for example 149, is known with a reasonable certainty to be within the volume 29 on the other side of the membrane. That placement having been accomplished, the connecting portion between an adjacent pair of swellable parts (between 142 and 144 in FIG. 16) is certain to traverse the rent. Then, as the swellable parts of the plug 160 swell, the medial regions 173, 175 of the swelling parts 172, 174 engage the edge 26 of the rent as shown in FIG. 17 and swell further so that medial portions 183, 185 of swollen parts 182, 184 engage the surfaces of the membrane at the margins of the rent, securing the barrier 180, as shown in FIG. 18.

Figure 12:
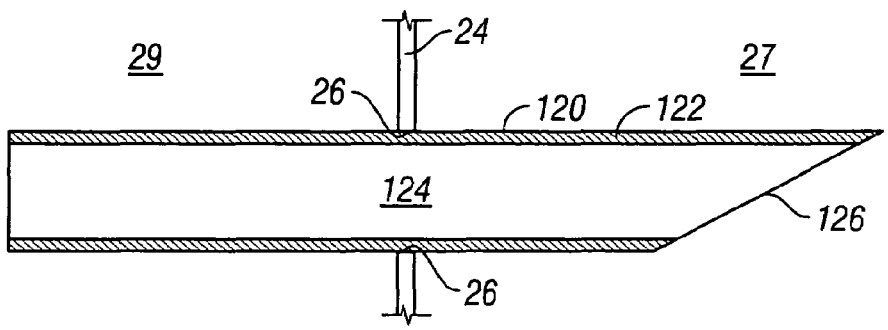
FIGS. 12–15 are diagrammatic sketches in a lengthwise sectional view showing stages in placement of a plug at a dural puncture site according to an embodiment of the invention.
Figure 13:
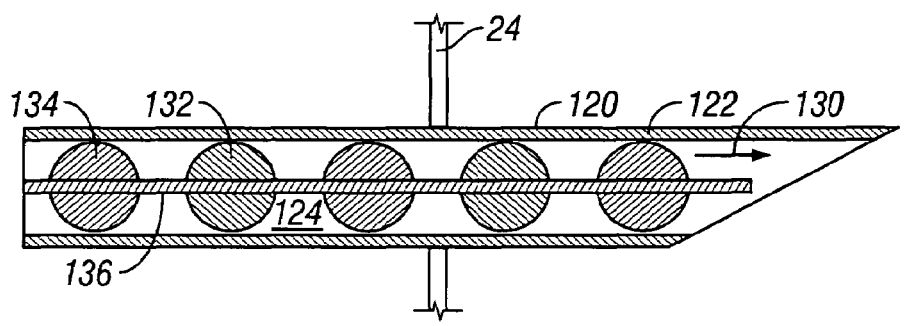
Figure 14:
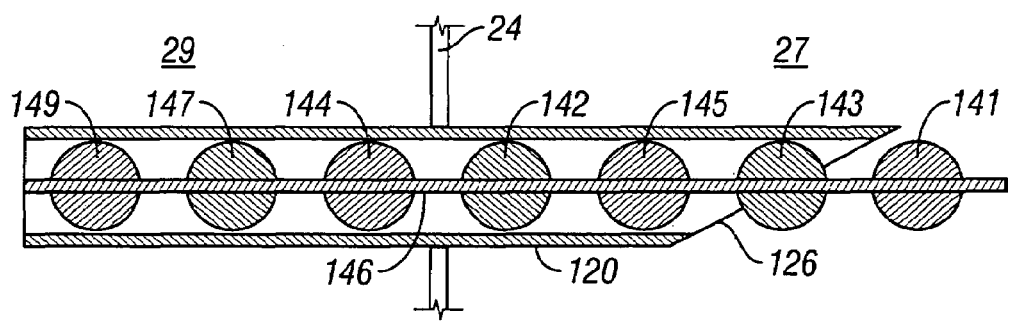
Figure 15:
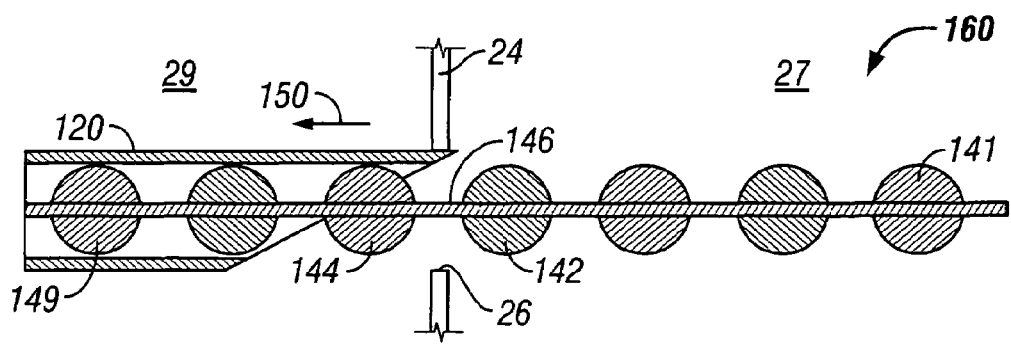

Placement of a plug 160 according to one embodiment of the invention is illustrated in FIGS. 12 through 15. In FIG. 12 a dural needle 120 is shown, having a wall 122 and a lumen 124, and having an angled bevel 126 at the tip. Techniques are well known for insertion of such a dural needle so that the tip is placed for access to the cerebrospinal fluid within the subarachnoid space 27. The needle passes through (among other anatomical features) the epidural space 29 and the dura 24, in which the needle cuts an edge 26 defining a dural puncture. Generally, the operator can feel the puncture of the dura as the needle is forced through it (sometimes referred to as the dural "pop"), and care is taken as a matter of course not to advance the tip of the needle more than a few millimeters (or less) beyond that point. The needle 120 is placed for any of a variety of purposes that call for access to the cerebrospinal fluid in the subarachnoid space: withdrawal of a sample of CSF, for example, or introduction of an anesthetic. According to the invention, the dural plug can be inserted by way of the lumen 124 of the same needle 120 whose deployment created the dural puncture. A dural plug as shown for example in any of FIG. 3, 6, 9 or 16 (or other configuration within the scope of the invention) can be inserted within the lumen 124; FIGS. 13–15 illustrate placement of a plug having several swellable parts serially spaced on a filament, as described above with reference to FIG. 16.

With the needle 120 deployed, as described with reference to FIG. 12, the plug 160 is passed within the lumen 124 toward the tip of the needle 120, as indicated by arrow 130 in FIG. 13. As shown in FIG. 13, the plug 160 includes several swellable parts (e.g., 132, 134) affixed at intervals on a filament 136. The filament 136 is sufficiently stiff that it serves to maintain the spacing and the axial alignment of the swellable parts as the plug is passed through the needle. A separate stylet or other pusher (not shown) may be employed to press the plug through the needle. Or, a proximal extended length of the filament (not shown in FIGS. 13–18) may serve as a stylet, as described with reference to FIG. 9. The pusher or stylet or extended length of the filament may be marked with length indicia, so that the progress of the plug toward the tip of the needle may be monitored. The plug is advanced until, as is shown for example in FIG. 14, the operator is reasonably certain that at least the most distal swellable part 141 is inside the membrane (within the subarachnoid space in this illustration) and that at least one more proximal swellable part (e.g., 149) is within a section of the needle that is outside the membrane (in the epidural space in this illustration). This can be accomplished, for example, by employing a plug whose swellable portion (series of swellable parts) has an overall length greater than any likely distance that the tip of the needle is deployed beyond the membrane, and advancing the plug within the needle just to the point that the most distal swellable part 141 is located approximately at the tip, as illustrated in FIG. 14.

Then the needle is withdrawn as indicted by the arrow 150 in FIG. 15, while the position of the plug 160 is maintained. As will be apparent, if the needle were deployed more or less deeply beyond the rent than is shown in this illustration, or if the plug were advanced more or less far within the needle than is shown, then a different connected pair of swellable portions would have come into play in the formation of the barrier. Although the operator cannot determine precisely where along the length of the plug a connecting part between an adjacent pair of swellable portions will traverse the rent, it is reasonably certain that such will somewhere occur, in a connecting portion (146 as illustrated here) between some pair (here 142, 144) of adjacent swellable parts between the most distal one (141) and the more proximal one (e.g. 149). The swellable parts of the plug swell in situ to form the barrier as described above with reference to FIGS. 16–18.

Figure 20:
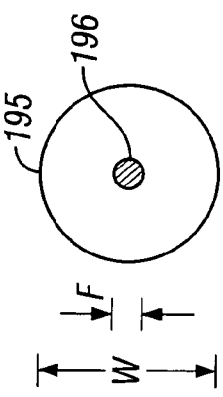
FIGS. 19–20 are diagrammatic views in sectional views thru a portion of a plug according to the invention, marked for reference to dimensions.
Figure 19:
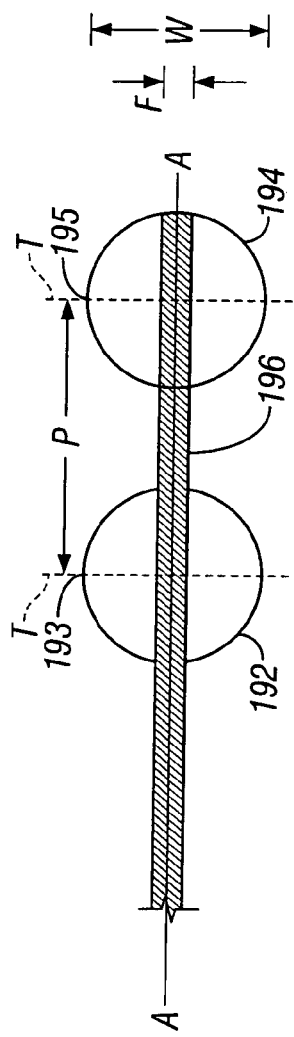

The plug is represented in the foregoing Figs. as having spheroidal or spherical swellable parts or beads. FIGS. 19 and 20 are sectional views showing a portion of such a plug 190, including several swellable parts and connecting parts between them, marked for illustration of a range of dimensions that the various features of the plug may have according to the invention. FIG. 19 is a lengthwise sectional view made along an axis A defined by the centerline of the connecting part or filament 196, and FIG. 20 is a sectional view through a swellable part or bead (e.g., 192 or 194) in a plane transverse to the axis A. The connecting part or filament 196 has a diameter F, and the swellable parts or beads 192, 194 have a transverse width W as measured in the plane T transverse to the axis A. Adjacent swellable parts or beads 192, 194 are spaced apart by a pitch P measured lengthwise between respective points 193, 195 of greatest transverse width.

Where the plug is to be deployed by passing a within the lumen of the needle or catheter, the transverse width W is determined by the lumenal dimension, that is, by the inside diameter of the needle or catheter. Generally, the greatest transverse width W must be somewhat smaller than the inside diameter, so that the plug may be passed through the lumen of the needle or catheter with little or no frictional resistance. The dimensions of the defect in the membrane depend particularly upon the outside diameter of the needle that was used to create the puncture, as well as the configuration of the tip of the needle and technique employed. In order to form a secure barrier, the deployed plug will have to be capable of swelling to engage the membrane at the rent, as described with reference to for example to FIGS. 4 and 5. Accordingly, it can be advantageous to use a plug having the largest transverse width W that can pass the lumen of the needle, and to select a needle having a thinner wall than a thicker wall. And, accordingly, it can be advantageous to form the swellable parts or beads of the material having a greater rather than a lesser dimensional swell capacity.

The pitch P is determined by consideration of the size of the swellable parts or beads and of the dimensional swell capacity of the material of which they are made. That is, referring again to FIGS. 3–5, the pitch is determined such that as the swellable material swells (FIG. 4) the medial regions 43, 45 of the swelling parts 42, 44 swell against the surfaces of the membrane 24 at the edge of the rent, and then continue to swell (FIG. 5) until the medial regions 53, 55 of the swelling parts 52, 54 engage the surfaces of the membrane at the margin of the rent, securing the barrier. If the swellable parts or beads are made of a material having a lower dimensional swell capacity, then the beads can be pitched closer together to achieve this result.

The series of swellable parts or beads constitute the swellable portion 191 of the plug 190. The length L of the swellable portion 191 of the plug 190 is determined by the number of swellable parts or beads and by the spacing between them. As explained above with reference to FIGS. 12 to 18, the length L is selected to assure that, within a reasonable certainty, the connecting part between an adjacent pair of swellable parts or beads will traverse the rent following deployment of the plug at the site. That is, given a preferred pitch P, the swellable portion of the plug will include a sufficient number of swellable parts or beads to provide a length L that will span the greatest likely margin of error in positioning the plug at the site.

As noted earlier, the swellable parts of the plug according to the invention may have any of a wide variety of shapes. What is required is that at least two connected wider swellable parts have a narrower region between them, so that the plug can be placed at the rent site such that the wider parts are situated on opposite sides of the membrane or wall, with the narrower region traversing the rent.

FIGS. 21–30 show a few illustrative examples of suitable configurations. For ease of reference, each of FIGS. 21, 23, 25, 27 and 29 is a side view of a portion of two connected wider adjacent swellable parts or beads of a plug body according to an embodiment of the invention, and each of FIGS. 22, 24, 26, 28 and 30 is an axial view (along A—A taken as indicated) of one of the wider swellable parts or beads. In each of FIGS. 21, 23, 25, 27 and 29, T indicates a plane transverse to the axis A—A at the place where the width of a wider swellable part or bead is greatest, and only that portion of the swellable parts or beads that is between the planes T is shown. In each embodiment, the plug is narrower between the wider swellable parts or beads. Also, is was described earlier, the swellable portion of a plug according to the invention may have more than two wider swellable parts or beads, although portions of only two adjacent ones are shown here. As may be appreciated, each wider swellable part or bead may be symmetrical with respect to the plane T, but it is not necessarily so; also, adjacent wider swellable parts or beads may be similarly shaped, as is shown in these Figs., but adjacent wider swellable parts or beads may according to the invention be shaped differently.

Figure 21:
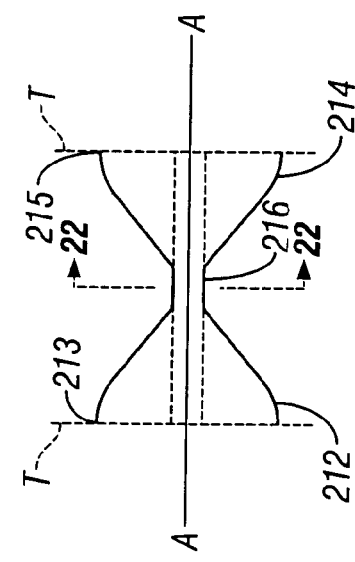

By way of example, FIG. 21 shows a portion of two swellable beads 212, 214 connected on a non-swellable filament 216. Each bead is elongated axially toward the adjacent bead, so that each bead tapers from its wider point 213, 215 toward the filament 216. In such an embodiment, as in the embodiment shown in FIGS. 19 and 20, the narrower region between the wider points of the beads is the diameter of the filament; but in this embodiment a transition between the wider and narrower regions is more gradual than is provided by the spherical or spheroidal bead configuration as in FIG. 19.

Figure 23:
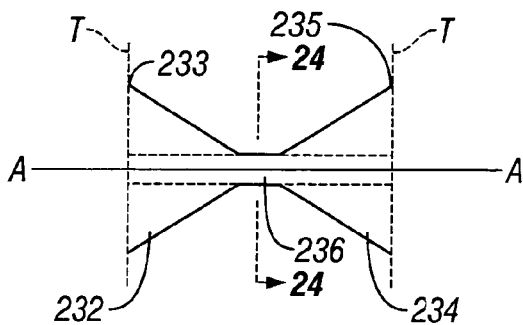

Rather than being rounded in side view at its widest point, as shown for example in FIG. 21, each bead may have an edge or rim, as shown for example in FIG. 23. In this example each of the illustrated bead portions 232, 234 is generally conical, tapering from its widest point 233, 235 toward the filament 236. In an example such as this, in the case where the plug is deployed with the opening in the membrane very close to the widest point of a bead, the plug may self-adjust as it swells, moving axially in one direction or the other to capture the membrane or wall between adjacent beads more effectively than would a plug having a more rounded configuration as shown for example in FIG. 19 or FIG. 21. In this embodiment, as in an embodiment as shown for example in FIG. 21, the narrower region between the adjacent beads is the diameter of the filament.

Figure 25:
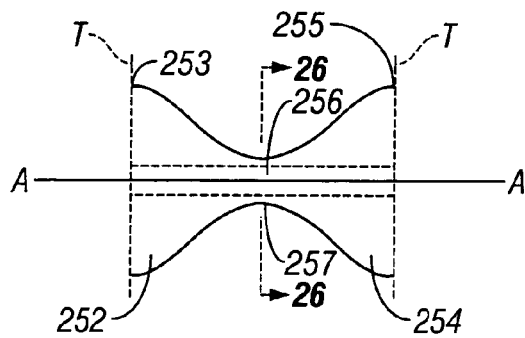

As illustrated for example in FIG. 25, the narrower region 257 between adjacent wider swellable parts 252, 254 may, in some embodiments, have swellable material surrounding the filament 256. This may increase the capacity of the swellable material to effectively fill the rent, particularly in applications where the wall or membrane is thicker and the beads or wider swellable portions are more widely spaced apart. That is, it is not necessary nor is it in some applications desirable that the narrower region be as narrow as the filament; in practice it need only be narrow enough to permit the adjacent swellable parts to engage the surfaces of the wall or membrane at the margin of the rent, and thereby securing the barrier in place within the rent site.

Figure 22:
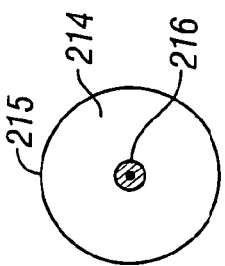
FIGS. 21–30 are diagrammatic sketches in side views (21, 23, 25, 27, 29) and axial views (22, 24, 26, 28, 30) of portions of plugs in various configurations according to the invention.
Figure 24:
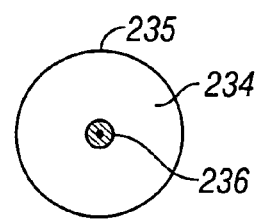
Figure 26:
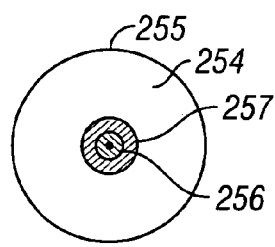
Figure 27:
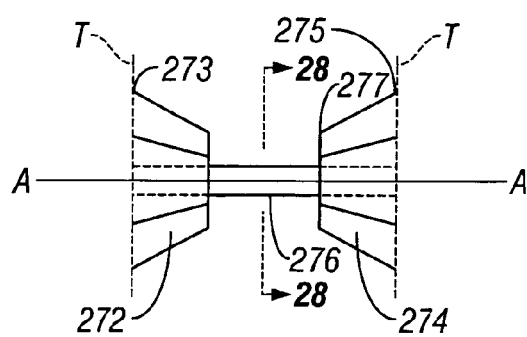
Figure 28:
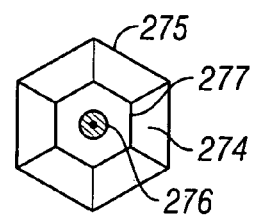

FIGS. 22, 24 and 26 show the bead as circular at its widest point and centered at the axis of the filament. It may according to the invention be round or rounded yet non-circular, for example oval or ovoid. Or, other shapes are possible according to the invention, as FIGS. 27–30 show by way of illustration.

Figure 29:
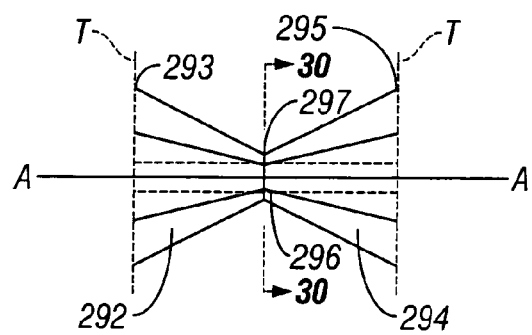
Figure 30:
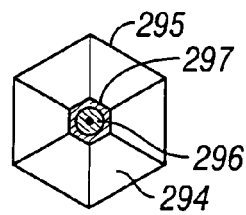

In the examples shown in FIGS. 27–30, rather than having a circular transverse section, each bead may have a polygonal shape at its widest point (hexagonal in the Figs., by way of example), so that each of the illustrated bead portions has a pyramidal or truncated pyramidal shape. Thus, each of bead portions 272, 274 in FIGS. 27 and 28 has a polygonal (hexagonal) shape at the wider point 273, 275 and then tapers as a pyramid to a truncation point, e.g., 277. The narrower point in this embodiment is the diameter of the filament 276, and the filament 276 is bare over a significant part of the separation between the beads, and in this respect is similar to a configuration having spheroidal beads on a filament as illustrated in FIG. 19. In FIGS. 29 and 30 each of bead portions 292, 294 has a polygonal (here hexagonal) shape at the wider point 293, 296 and then tapers as a truncated pyramid; but here the pyramids meet at the narrower point 297, to provide some swellable material surrounding the filament 296.

Still other shapes are contemplated according to the invention. As will be appreciated, the wider swellable portions need not be as regularly shaped as illustrated here, nor need they be precisely formed.

Generally, the invention can be useful in surgical procedures in the fields of endoscopy, laparoscopy, orthoscopy, bronchoscopy, and others. For example, the aorta may be accessed from within the stomach by way of a puncture through the stomach wall, using an esophageal endoscope; according to the invention, a barrier can be formed in the rent in the stomach wall at the completion of the procedure. Similarly, in circumstances in which a transurethral catheter cannot be placed, a superpubic puncture of the urinary bladder may be made; a barrier can be formed according to the invention to prevent leakage of urine into the peritoneal cavity through the rent in the bladder wall.

The invention can also be employed in conjunction with any of a variety of medical procedures in which a puncture or rent is formed unintentionally. For example, an unintentional puncture may occur in the course of any of various minimally invasive procedures involving access by way of the lumen of a hollow organ of the body, as for example in various procedures in urology or gastroenterology; such complications are regrettably high, but can be mitigated by using a barrier formed according to the invention to control movement of fluids or fluid-borne materials through the puncture.

Other embodiments are within the following claims.

What is claimed is:

1. A method for limiting fluid movement through a rent in a membranous tissue in a body, wherein the membranous tissue comprises a dura mater and the rent is a dural defect, comprising placing within the rent a plug that includes connected water-swellable parts.

2. The method of claim 1 wherein the plug comprises two swellable parts joined by a connector, and placing the plug within the rent comprises positioning the plug so that one swellable part is within a volume bounded by a surface of the membranous tissue and the other swellable part is within a volume bounded by an opposite surface of the membranous tissue, and the connector traverses the rent.

3. The method of claim 1 wherein the plug comprises a swellable portion comprising a plurality of swellable parts joined by a connector, and placing the plug within the rent comprises positioning the plug so that at least a first one of the swellable parts is within a volume bounded by a surface of the membranous tissue and at least a second one of the swellable parts is within a volume bounded by an opposite surface of the membranous tissue, and the connector traverses the rent.

4. The method of claim 1, further comprising forming a pathway to the rent, wherein placing the plug within the rent comprises passing the plug along the pathway to the site of the rent.

5. The method of claim 4 wherein forming the pathway comprises introducing a blade from an introduction site through intervening tissue to the site of the rent, and withdrawing the blade.

6. The method of claim 4 wherein forming the pathway comprises introducing a probe from an introduction site through intervening tissue to the site of the rent, and withdrawing the probe.

7. The method of claim 1 wherein placing the plug within the rent comprises passing the plug to the rent within a lumen of a needle extending from an introduction site through intervening tissue to the site of the rent.

8. The method of claim 1 wherein placing the plug within the rent comprises passing the plug to the rent within a lumen of a catheter extending from an introduction site through intervening tissue to the site of the rent.

9. The method of claim 8 wherein the rent is an intraspinal dural defect.

10. The method of claim 8 wherein the rent is an intracranial dural defect.

11. The method of claim 10, further comprising forming a pathway to the rent, wherein placing the plug with the rent comprises passing the plug along the pathway to the site of the rent.

12. The method of claim 11 wherein forming the pathway comprises introducing a blade from an introduction site through intervening tissue to the site of the rent, and withdrawing the blade.

13. The method of claim 11 wherein forming the pathway comprises introducing a probe from an introduction site through intervening tissue to the site of the rent, and withdrawing the probe.

14. The method of claim 1 wherein the rent is an intraspinal dural defect.

15. The method of claim 1 wherein the rent is an intracranial dural defect.

16. A method for limiting fluid movement through a rent in the spinal dura mater, comprising providing a plug comprising swellable parts joined by a connector, and placing the plug within the rent such that at least one of the swellable parts is within a subarachnoid space and at least one other one of the swellable parts is positioned in an epidural space, and the connector traverses the rent in the dura mater.

17. The method of claim 16 wherein the plug comprises two swellable parts joined by a connector, and placing the plug within the rent comprises positioning the plug so that one swellable part is within a volume bounded by a surface of the dura mater and the other swellable part is within a volume bounded by an opposite surface of the dura mater, and the connector traverses the rent.

18. The method of claim 16 wherein the plug comprises a swellable portion comprising a plurality of swellable parts joined by a connector, and placing the plug within the rent comprises positioning the plug so that at least a first one of the swellable parts is within a volume bounded by a surface of the dura mater and at least a second one of the swellable parts is within a volume bounded by an opposite surface of the dura mater, and the connector traverses the rent.

19. The method of claim 16 wherein placing the plug within the rent comprises passing the plug to the rent within a lumen of a needle extending from an introduction site through intervening tissue to the site of the rent.

20. The method of claim 19 wherein the rent is an intraspinal dural defect.

* * * * *